United States Patent [19]

Chalk

[11] Patent Number: 4,910,346

[45] Date of Patent: Mar. 20, 1990

[54] 3-(3-PROPAN-2-YLPHENYL)BUTANAL AND 3-(3-PROPEN-2-YLPHENYL)BUTANAL

[75] Inventor: Alan J. Chalk, Kinnelon, N.J.

[73] Assignee: Givaudan Corporation, Clifton, N.J.

[21] Appl. No.: 269,516

[22] Filed: Nov. 10, 1988

[51] Int. Cl.$^4$ .................... C07C 47/542; A61K 7/46
[52] U.S. Cl. .................................. 568/425; 512/21; 512/27
[58] Field of Search .................. 568/425; 512/12, 21

[56] References Cited

U.S. PATENT DOCUMENTS

| | | | |
|---|---|---|---|
| 1,844,103 | 2/1932 | Knorr et al. | 568/425 |
| 2,875,131 | 2/1959 | Carpenter et al. | 568/425 |

FOREIGN PATENT DOCUMENTS

| | | | |
|---|---|---|---|
| 1145161 | 3/1963 | Fed. Rep. of Germany | 568/425 |
| 2952719 | 7/1981 | Fed. Rep. of Germany | 512/21 |
| 0035140 | 3/1981 | Japan | 512/21 |
| 7905175 | 1/1981 | Netherlands | 512/21 |

OTHER PUBLICATIONS

H. A. Colvin et al., Chemtech 15, (1986), 500–504.
W. Berends et al., P. & E. O. R. 58, (1967), 372–378.

*Primary Examiner*—Werren B. Lone
*Attorney, Agent, or Firm*—Robert F. Tavares; Linda A. Vag

[57] ABSTRACT

The novel odorants, 3-(3-propan-2-ylphenyl)butanal and 3-(3-propen-2-ylphenyl)butanal, are disclosed.

4 Claims, No Drawings

3-(3-PROPAN-2-YLPHENYL)BUTANAL AND 3-(3-PROPEN-2-YLPHENYL)BUTANAL

SUMMARY OF THE INVENTION

This invention concerns the novel odorants 3-(3-propan-2-ylphenyl)butanal (1a) and 3-(3-propen-2-ylphenyl)butanal (1b) which can be represented by the formula

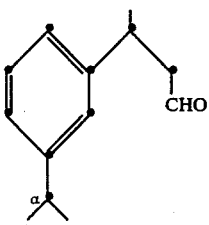

I wherein the dotted line, a, represents an optional bond.

The compounds of the present invention have odors which can be described as fresh, floral, fruity, melon having qualities found in lily-of-the-valley (muguet) and linden blosson. They are useful as odorants and may be used in perfumes, colognes, soaps, detergents, cosmetics and other toilet goods.

DESCRIPTION OF THE PREFERRED EMBODIMENTS

The novel compounds of the present invention can be prepared according to Scheme 1.

SCHEME I

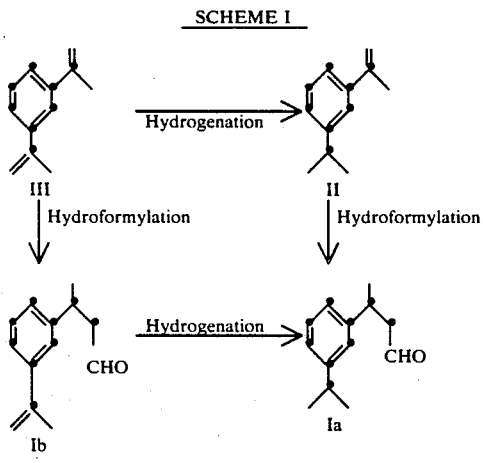

As illustrated in Scheme 1, the novel compounds of this invention can be prepared from the readily available m-diisopropenylbenzene, lll. (The starting material lll is commercially available or may be prepared by known methods, e.g., see H. A. Colvin and J. Muse, Chemtech 15, (1986) 500–4.) The 3-(3-propen-2-ylphenyl)butanal, 1b, can be prepared by hydroformylation of the starting material, lll, as shown in Scheme 1 and illustrated by Example 1. It is preferred to prepare the compound 1a, via the hydrogenation of 1b, also shown in Scheme 1 and illustrated by Example ll. An alternate synthesis of 1a involves reducing one of the olefinic bonds of lll to form ll and then converting ll to 1a via hydroformylation.

Compounds 1a and 1b have fresh, floral, fruity, melon odors with qualities of lily-of-the-valley and linden blossom which makes them particularly valuable in perfumery. They are most useful in providing a natural floral quality and lift to fragrance bases. The fresh quality which may be described as ozone-like, is more predominant in compound 1b, whereas in compound 1a, the floral character is more predominant.

Compound 1a, which has a fine, floral, melon odor is the more preferred compound of the invention. It has those qualities found in lily-of-the-valley and linden blossom to a greater degree than 1b. The compound is powerful and diffusive and can be used widely for floral effects and to give long lasting fresh, green topnotes. It is useful for lilac, rose, lily, peony, magnolia, orange blossom and other related fragrances.

Compound 1b has a floral stemmy-green, melon odor with a clean, ozone character. Its odor notes make 1b particularly useful in citrus, green-herbal and floral aldehyde fragrance compositions.

The compounds can be used in fragrances in the ratio of about 1 to 200 parts per thousand of the odorant composition containing the compound. A range of 50 to 100 parts is preferred for most compositions. Larger quantities, e.g., 200–900 parts can be used to achieve special effects.

The odorant compositions containing the compounds of this invention can be used as odorant bases for the preparation of perfumes and toilet waters by adding the usual alcoholic and aqueous diluents thereto; approximately 15–20 percent by weight of base would be used for the former and approximately 3–5 percent by weight would be used for the latter.

Similarly, the base compositions can be used to odorize soaps, detergents, cosmetics, or the like. In these instances a basic concentration of from about 0.5 to about 2 percent by weight can be used.

The following Examples are provided to illustrate further the practice of the present invention. They are for purposes of preferred embodiments only and should not be construed as limiting.

EXAMPLE I

Preparation of 3-(3-propen-2-ylphenyl)butanal, 1b.

m-Diisopropenylbenzene (237 g), 0.2 g butylated hydroxytoluene, 0.1 g $NaHCO_3$, 0.0918 g $RhHCO(PPh_3)_3$ and 20 g triphenylphosphine were heated under a pressure of 250 psi hydrogen and 250 psi carbon monoxide at 110° C. for five hours and then at 140° C. for six hours. The crude reaction product was distilled to give 215 g of a liquid which analyzed as 49.4% starting material, 40.8% 1b, 1.9% 2-(3-propenylphenyl)-2-methylpropanal and 4.9% 1,3-di-(1-formylpropan-2-yl)benzene. The constituents were readily separated by fractional distillation to give pure 1b, b.p 98° C./0.1 mm Hg. The starting material may be recycled to give further product in an overall yield of 71.0% 1b. IR and NMR spectra were compatible with the assigned structure. Odor: ozone, stemmy-green floral, melon. Odor value: 35,514; Odor threshold value: 0.7 ng/L.

EXAMPLE II

Preparation of 3-(3-propan-2-ylphenyl)butanal, 1a.

3-(3-Propen-2-ylphenyl)butanal, 1b, (100 g) was hydrogenated over palladium on charcoal (5% wet, 1 gram) in 150 ml ethanol for 2.5 hours at 50 psi hydrogen using a Parr-shaker apparatus. The product mixture was decanted, filtered and the ethanol removed on a rotary evaporator to give 97 grams of a mixture which analyzed as 95.8% 1a, and 2% 1b. The mixture was distilled to give 78.1 g pure 1a, b.p. 84° C./0.3 mm.Hg. Yield 78.0% 1a. IR and NMR spectra were compatible with the assigned structure. Odor: fresh, floral, melon having qualities found in lily-of-the-valley (muguet) and linden blossom. Odor value: 981,483; Odor threshold value: 0.07 ng/L. EXAMPLE III Muguet Fragrance with 15% 1a for soap bar Without 1a the composition was found to be of moderate intensity and somewhat unblended in that the rose notes dominated. The addition of 1a improved the floral character of the composition by contributing a watery or dewy quality, an effect which changes the impression from rose to lily-of-the-valley making the composition more natural and reminiscent of the flower. 1a made the odor effect markedly stronger.

| Component | Parts |
| --- | --- |
| Phenylethyl alcohol | 200 |
| Citronellol | 300 |
| Geraniol | 150 |
| Benzyl Acetate Extra | 60 |
| Nonane-1,3-diol acetate | 10 |
| Amyl Cinnamic Aldehyde | 75 |
| Aldehyde C-14 | 4 |
| Heliotropin | 50 |
| 1a | 150 |
| Dipropylene glycol | 1 |
|  | 1,000 |

EXAMPLE IV

Citrus Fragrance with 10% 1a for cleaning products

Without 1a the composition was found to be of moderate intensity. With the addition of 1a the intensity was enhanced and a tartness was added which makes the citrus fragrance fresher, stronger and a more desirable citrusy odor type.

| Component | Parts |
| --- | --- |
| Bergamot Synthetic | 200 |
| Citron Synthetic | 400 |
| Geranyl Nitrile | 5 |
| Geraniol | 100 |
| Litsea Cubeba | 10 |
| Cyclohexanol, 4-(1,1-dimethylethyl)-, acetate | 50 |

| Component | Parts |
| --- | --- |
| Anthranilic acid, N—[3-(1,1-dimethylethyl)phenyl]-2-methylpropylidene-,methyl ester | 5 |
| Eucalyptol | 10 |
| 1a | 100 |
| Dipropylene glycol | 120 |
|  | 1,000 |

EXAMPLE V

Rose Musk fragrance with 2% 1a

Without 1a the woody and musky notes stood out from the composition. The addition of 1a is added a strong floral quality to the fragrance which complimented the woody and musky odors. The fragrance with 1a is brighter, fresher, and stronger than the fragrance without 1a.

| Components | Parts |
| --- | --- |
| Geranium Bourbon | 15 |
| Linalool | 50 |
| Rhodinol Pure | 50 |
| Methyl ionone | 60 |
| 1-(2,6,6-Trimethyl-2-cyclohexen-1-yl)-hepta-1,6-dien-3-one | 5 |
| Methyl Cedryl Ketone | 150 |
| Heliotropin | 40 |
| Coumarin | 70 |
| 4-t-Butyl-3,5-dinitro-2,4-dimethylacetophenone | 50 |
| Cinammic Alcohol | 5 |
| Vanillin | 10 |
| Sandela ® (Givaudan) (iso-camphylcyclohexanols) | 150 |
| Crysolide ® (Givaudan) (4-Acetyl-6-t-butyl-1,1-dimethylindane) | 100 |
| Synthetic Rose Base | 140 |
| Synthetic Civet Base | 1 |
| 1a | 20 |
| Dipropylene glycol | 84 |
|  | 1,000 |

I claim:
1. 3-(3-propan-2-ylphenyl)butanal.
2. 3-(3-propen-2-ylphenyl)butanal.
3. A fragrance composition comprising an olfactorily effective amount of 3-(3-propan-2-ylphenyl)butanal and at least one other odor imparting substance.
4. A fragrance composition comprising an olfactorily effective amount of 3-(3-propen-2-ylphenyl)butanal and at least one other odor imparting substance.

* * * * *

UNITED STATES PATENT AND TRADEMARK OFFICE
CERTIFICATE OF CORRECTION

PATENT NO. : 4,910,346

DATED : March 20, 1990

INVENTOR(S) : Alan J. Chalk

It is certified that error appears in the above-identified patent and that said Letters Patent is hereby corrected as shown below:

Column 1, lines 10-20, formula I, correct

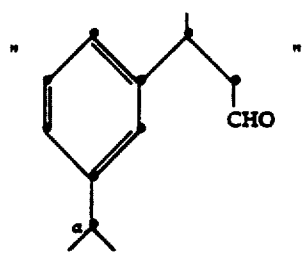

UNITED STATES PATENT AND TRADEMARK OFFICE
CERTIFICATE OF CORRECTION

PATENT NO. : 4,910,346

Page 2 of 2

DATED : March 20, 1990

INVENTOR(S) : Alan J. Chalk

It is certified that error appears in the above-identified patent and that said Letters Patent is hereby corrected as shown below:

to read

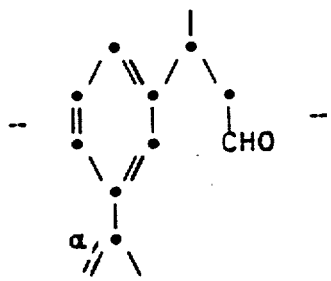

Signed and Sealed this

Twenty-eighth Day of January, 1992

Attest:

HARRY F. MANBECK, JR.

Attesting Officer

Commissioner of Patents and Trademarks